United States Patent [19]

Sipin

[11] Patent Number: 5,405,251
[45] Date of Patent: Apr. 11, 1995

[54] OSCILLATING CENTRIFUGAL PUMP

[76] Inventor: Anatole J. Sipin, 221 E. 78th St., New York, N.Y. 10021

[21] Appl. No.: 950,090

[22] Filed: Sep. 11, 1992

[51] Int. Cl.[6] ............................................ F04B 17/00
[52] U.S. Cl. ............................... 417/420; 417/423.1; 417/423.7; 415/146
[58] Field of Search ................. 417/50, 352, 353, 354, 417/410 R, 423.1, 423.7, 424.1, 420; 415/146, 70

[56] References Cited

U.S. PATENT DOCUMENTS

| | | | |
|---|---|---|---|
| 3,173,656 | 3/1965 | Prees | 417/352 |
| 4,164,690 | 8/1979 | Muller et al. | 417/423.7 |
| 4,304,532 | 12/1981 | McCoy | 417/420 |
| 5,017,103 | 5/1991 | Dahl | 417/423.7 |
| 5,112,202 | 5/1992 | Oshima et al. | 417/423.7 |
| 5,253,986 | 10/1993 | Bond et al. | 417/420 |

FOREIGN PATENT DOCUMENTS 1124752  4/1955  France .................... 415/146

*Primary Examiner*—Richard A. Bertsch
*Assistant Examiner*—William Wicker
*Attorney, Agent, or Firm*—Hedman, Gibson & Costigan

[57] ABSTRACT

An oscillating centrifugal pump is disclosed which has a housing, an impeller and a magnetic drive. The housing has a longitudinal axis, having a front end and a rear end that are spaced apart on the longitudinal axis. The housing includes a pumping chamber within and at the front end of the housing. The pumping chamber is created by a continuous transverse front wall that closes the pumping chamber at the front end of the housing, a transverse rear wall axially-spaced from said transverse front wall and has a central opening, and a longitudinal closed side wall which is between the front and rear transverse walls. The housing is closed except for an inlet in the housing that is outside of and is axially spaced from the pumping chamber. An outlet is provided in the longitudinal side wall of the pumping chamber, and the housing is free of mechanical bearings, flexing or external seals or apertures that lead to the exterior of the housing except for said inlet and outlet. The impeller is located in the pumping chamber and has an axial inlet and a radial outlet and a flow passage between the impeller inlet and outlet. The impeller is mounted on an elastic support, which provides limited freedom of angular oscillation for the impeller about the longitudinal axis of the housing.

19 Claims, 12 Drawing Sheets

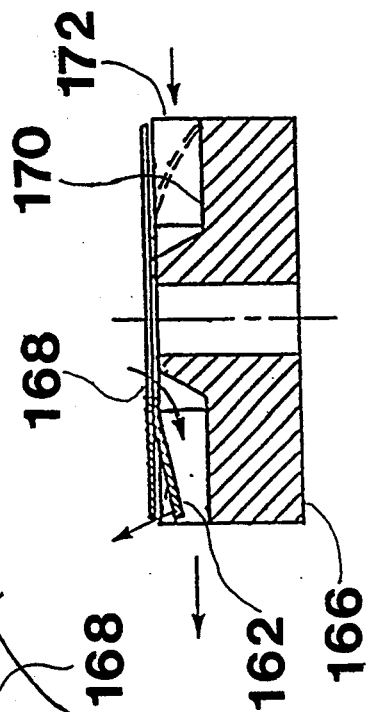
FIG. 21
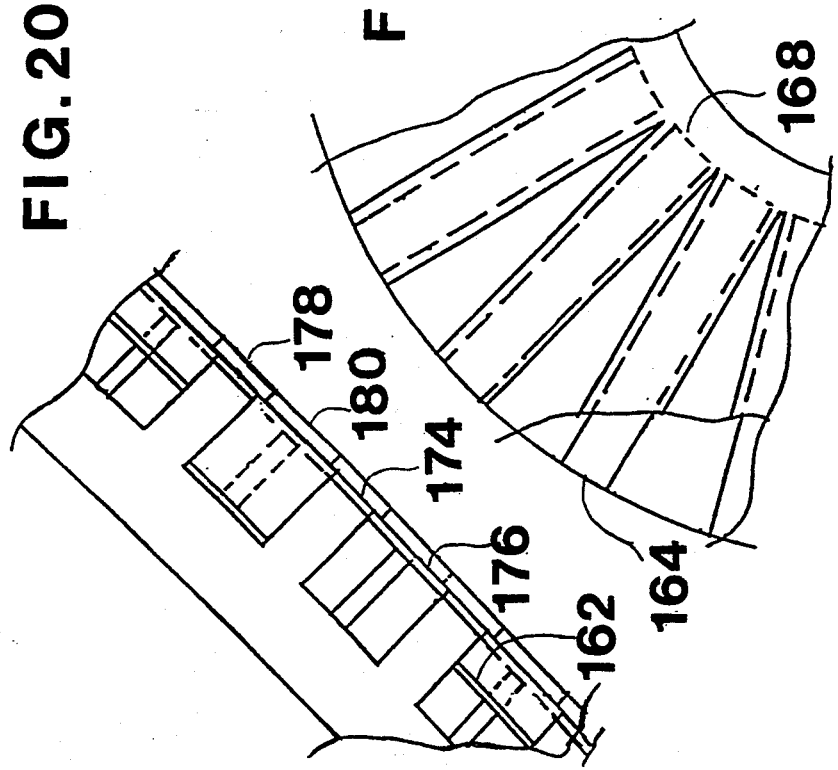
FIG. 19
FIG. 20

OSCILLATING CENTRIFUGAL PUMP

BACKGROUND OF THE INVENTION

The disclosed invention is a fluid pump having an easily replaceable pumping element that is free of bearings, frictional contact or rotating parts in the flow path, and that is also free of bearings, flexing seals or apertures leading to the exterior, except for the inlet and the outlet of the pumping element. While the new pump will be advantageous in many applications where leakage, fluid contamination and damage by or to the fluid are objectionable, such as pumping pharmaceuticals and biological and sanitary fluids, a major application will be as a blood pump for circulatory assist and also for cardiopulmonary bypass.

There has been an increasing interest in continuous, rotary blood pumps for circulatory assist and circulation maintenance, to alleviate problems identified with displacement types of ventricular assist devices such as infection, thrombosts and control. There are also, however, mechanical problems with existing centrifugal (and other rotary) pumps, such as infection through shaft seal, possible seal leakage, thrombosts and blood injury in bearings.

The fact that such problems are still prevalent with rotary blood pumps, in spite of the large number of different developments that have taken place in recent years is attested to by reference to them in a number of papers presented at an International Workshop on Rotary Blood Pumps held in Baden, Austria Sep. 9–11, 1991. It was indicated that lack of a long-lived bearing is the principal obstacle to the use of a continuous rotary pump as an implanted assist device. It was also found that bearing seals in rotary blood pumps were apt to fail when immersed in blood. If there were no seal for a rotating bearing in a rotary blood pump, such problems would not exist.

It was also stated that blood leakage and thrombus formation about bearing or shaft seals still limit the clinical usage of centrifugal pumps, which require seals between the blood and bearings and actuators, and that commercially available disposable blood pumps can only be used on a patient for 48 hours before being replaced. The objective is for the development of a centrifugal blood pump which can provide over two weeks of continuous operation with an Inexpensive replaceable pumping element.

No practical, commercially available pump, based on oscillation of a centrifugal impeller within a replaceable pumping element suitable for blood pumping, and being free of bearings, flexing seals or external apertures is known to the applicant. U.S. Pat. No. 3,148,970 entitled "Method and Apparatus for Pumping Fluids by Oscillatory Impeller Action" and dated Aug. 11, 1964 discloses a separate oscillating pump driven by an oscillating electric motor through an external shaft that requires bearings and seals, and in which the system has ". . . longitudinally adjacent portions simultaneously torsionally elastically deformable in reverse directions about and with reference to an intermediate neutral portion . . ." The system disclosed is not adaptable for the pumping element to be contained in a sealed housing. U.S. Pat. Nos. 4,595,338 and 4,684,828 show bearing less fans using piezoelectric blades and U.S. Pat. No. 8,165,086 discloses an articulated fish-tail type of oscillating propeller for boats.

There is an evident need for an extracorporeal blood pump with a relatively long-lived, replaceable and inexpensive pumping element that has no bearings or frictional contacts within the element that could damage the blood, and no external apertures that could be paths for leakage or contamination.

SUMMARY OF THE INVENTION

The invention disclosed herein is an Oscillating Centrifugal Pump which provides improvements for pumping blood and other fluids where leakage to and contamination from the exterior, or where damage from or to the blood or other fluid by bearings in the fluid, can be detrimental.

Rotary blood pumps for circulatory assist and cardiopulmonary bypass contain bearings and external seals which limit the usage of replaceable pump heads due to thrombosts and blood leakage. The new oscillating centrifugal pump overcomes these limitations by eliminating any mechanical seal, either flexing or rubbing with the external environment and eliminating any frictional contact altogether.

A principal feature of all embodiments of the invention is that the pumping action is performed by a unitary, sealed, easily replaceable pumping element, which consists of a housing with a longitudinal axis, a pumping chamber at one end of the housing, an outlet in a wall of the pumping chamber, an inlet in the housing, axially spaced from the pumping chamber, an impeller in the pumping chamber, mounted on an elastic support which provides limited freedom of angular rotation for the impeller in either direction about the longitudinal axis, and magnetic means external to the housing to drive the impeller in an angular oscillation about the longitudinal axis within the pumping chamber by magnetic action through the walls of the housing. The sealed housing is free of bearings, flexing seals or apertures leading to the exterior of the housing except for the inlet and the outlet. The oscillating impeller contains a magnetic element, and it is driven in an angular oscillation by an external magnetic field to generate centrifugal pressure and flow. The pump housing, which contains only the impeller circulator and its support, is inexpensive and disposable.

In the preferred embodiment, the elastic impeller support is a torsion shaft with an oscillating end connected to the impeller and a stationary end connected to the housing. The shaft and the impeller form a spring-mass system with a torsional resonant frequency that is determined by the system stiffness and inertia. In the preferred embodiment the impeller Is mounted on a rotor that contains a magnet and is driven by stationary external electromagnetic coils. Delivery is controlled by varying the amplitude of the current passing through the coils at the torsional resonant frequency of the impeller and shaft.

In a variation of the magnetic driving means, it includes a stationary magnetic element, and the oscillating impeller rotor Includes an electromagnetic coil.

In a second variation, the impeller flow passages are pitched in one direction to provide a unidirectional component of tangential velocity to the fluid exiting the impeller.

In another variation the torsion shaft is replaced by a coil spring to provide a more compact assembly.

In a second embodiment of the Invention two oscillating centrifugal pump stages are hydraulically connected in series to form a two-stage oscillating centrifugal pump. The two stages can be oscillated in a 90 degree phase relation to eliminate reverse flow through an impeller at the end points of the oscillation cycle. The two stages can also be rigidly attached in opposition and operated in a 180 degree phase relation to cancel unbalanced oscillatory forces due to torsion of the elastic impeller supports.

In a final variation, check valve means are introduced in impeller flow passages to eliminate reverse flow at the oscillation end points.

BRIEF DESCRIPTION OF THE DRAWINGS

The following detailed description of the preferred embodiments can be understood better if reference is made to the drawings, in which:

FIGS. 19–21 explain the operation of another means of preventing backflow.

DETAILED DESCRIPTION OF THE INVENTION

Figure 1:
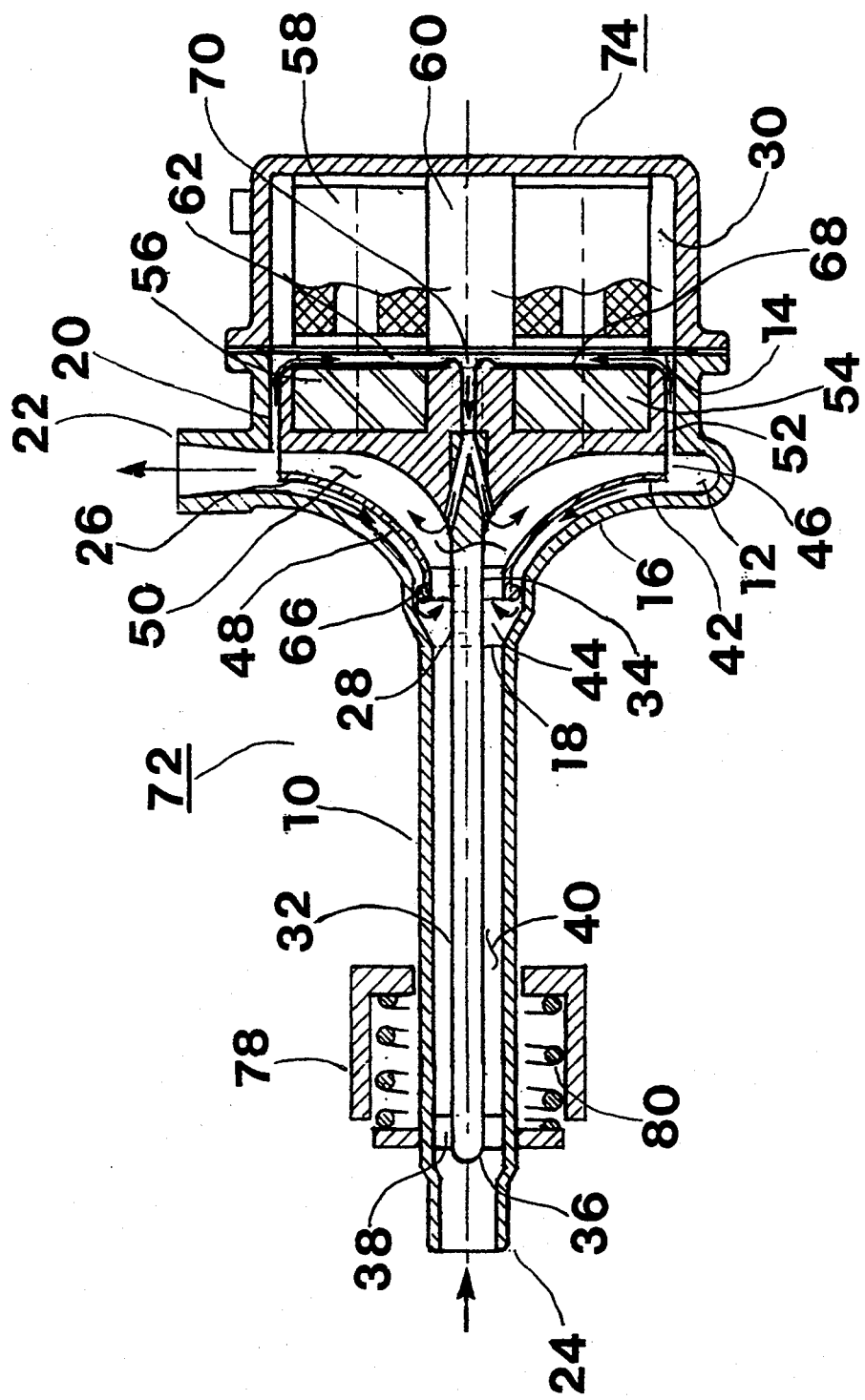
FIG. 1 is a sectional elevation view of the preferred embodiment of the invention illustrating the interactive relations among the major elements.

Referring to FIG. 1, the preferred Oscillating Centrifugal Pump includes a housing 10 with a longitudinal axis and a pumping chamber 12 located at the front end of the housing. The pumping chamber is defined by a continuous transverse front wall 14, which closes the pumping chamber at the front end of the housing, and a transverse rear wall 16 with a central opening 18, which is axially spaced from the continuous transverse wall 14, and a longitudinal co-axial side wall 20. An outlet 22 is located in the longitudinal wall 20 of the pumping chamber. An inlet 24 is located outside of and axially spaced from the pumping chamber toward the rear end of the housing. Between the front end and the rear end, the housing is continuous and integral, and it is free of bearings with sliding or rotating shafts, flexing seals or apertures leading to the exterior of the housing, except for inlet 24 and outlet 22. An impeller 26 is located in the pumping chamber. The impeller is mounted on an elastic support 28, which provides limited freedom of angular rotation for the impeller 26 in either direction about the longitudinal axis. The impeller is driven in an angular oscillation about the longitudinal-axis within the pumping chamber by magnetic action through the walls of the housing 10 from magnetic means 30 located external to the housing. As shown in FIG. 1, impeller support 28 is an elastic torsion shaft 82 with a front, oscillating, end 84 connected to the impeller 26 and a rear, stationary, end 86 connected to the housing 10 as a cantilever. The stationary end 86 of shaft 82 is built into a shaft support 38, which in turn is rigidly retained by housing 10. Shaft 82 and impeller 26 form a torsion spring-inertia system with a resonant frequency which is determined by the torsional stiffness of the shaft and the moments of inertia of the shaft and impeller assembly. For best performance the impeller and shaft must be driven at or near the resonant frequency, so as to achieve the maximum angular excursion of the impeller with minimum driving torque. Since the pressure generated by the oscillating impeller is determined by the tip velocity, it is desirable to achieve the highest resonant frequency that is consistent with an optimal impeller excursion and angular deflection of the shaft.

Outlet 22 is shown to have an axis that is normal to the oscillating path of impeller 26, which is consistent with radial or symmetrical flow passages in the impeller.

Inlet 24 is at the rear end of the housing 10 and coaxial with its longitudinal axis. To permit flow to pass from the inlet to the interior 40 of housing 10, shaft support 38 contains communicating flow passages.

Impeller 26 has a shroud or cover 42, which is used to minimize oscillating tangential shear stresses in the flow passages. The impeller inlet 44 is axial, and its outlet 46 is radial. On the shaft end 48 of the impeller there is a limited number of narrow flow channels 50. On the opposite end of the impeller is a magnetic rotor 52 containing magnets 54 and 56, which are driven by coils 58 in an axially spaced stator 60 to apply alternating torque to the oscillating assembly. The impeller and rotor, except for the magnets, could be made of rigid, lightweight plastic, such as polycarbonate (which also is blood compatible), to minimize weight and inertia of the oscillating parts. The spring could be made of -titanium alloy of high strength. Titanium is desirable because of high fatigue strength in shear, low modulus and low density.

Fluid flows into the pump inlet 24 on the left, axially past the torsion shaft 32, and then radially through the channels 50 into a partial collector and outlet. A channel is shown connecting the space in the gap 62 between the magnetic rotor 52 and the stator 60 on the right, and the impeller inlet 44, so as to provide a low recirculation which, if blood is pumped, will prevent stagnation and possible thrombosis. This may be an unnecessary precaution, as the high oscillatory velocities will preclude stagnant zones from forming.

Leakage flow exists between the oscillating cover 42 of the impeller 26 and the stationary housing wall 64. This flow is limited by a radial restriction 66 included in the axial inlet 44 to the impeller. A small clearance between the radial restriction and the axial housing wall limits the recirculation, and permits use of a larger, non-critical clearance between the impeller cover and the corresponding housing wall. Oscillatory shear stresses occur in a narrow layer at the surface of the impeller cover, but these affect a much smaller volume of flow than would be the case in an uncovered impeller, which experiences the entire flow volume. The leakage between the rear surface 68 of the rotor 52 and the continuous front wall 14 of the housing is limited by an axial restriction 70 located near the center of the rear rotor surface. A layer of high surface shear stress exists also on the rear surface of the rotor, but, as is the case for the front impeller cover, it affects only a small volume of flow.

As shown in FIG. 1, the oscillating centrifugal pump consists of a disposable oscillating pumping element 72, and a detachable and reusable drive unit 74, which contains the electrical drive coils 58. The front of the oscillating element assembly is permanently sealed from the detachable drive unit by transverse front wall 14. Assembly of the disposable element 72 is very simple. With the transverse front wall 14 removed, the rotor and torsion shaft assembly are introduced from the right into the housing 10 up to a stop at the extreme left. A shim is placed between the front wall 14 and the axial restriction 70 on the front surface 76 of the rotor 52 in order to control the axial restriction gap. The shaft and rotor assembly is then pushed to the right until contact is made with the shim, and the stationary shaft support 38 is anchored to the housing. The front wall 14 is then detached, the shim is removed, and the wall is replaced and permanently bonded to the disposable element housing 10. The front surface 76 Of the rotor 52 is covered with a protective coating (e.g. polyurethane) to isolate fluid from the magnets. The inlet gap with the radial restriction 66 at the inlet 44 of the impeller is determined by manufacturing tolerances. Since the lateral deflection of the torsion shaft 32 due to the weight of the rotor is on the order of one and one-half thousandths of an inch, the tolerances are not critical, and they are within the achievable tolerances of precision molded plastic parts. The inlet radial restriction 66 is not affected by axial positioning of the rotor and shaft assembly. The disposable pumping element 72 is fastened to the detachable drive unit 74 by screws in the corresponding flanges. A coaxial dynamic torsional vibration absorber 78 is located at the inlet end of the stationary housing 10 of the disposable pumping element 72. The absorber is shown using a coil spring 80, since there is greater leeway in design to provide absorption at the resonant frequency of the rotor. Overall dimensions for a typical pump assembly would be 6 in. length by 2.5 in. diameter (detachable drive unit).

Figures 2, 3, 4:
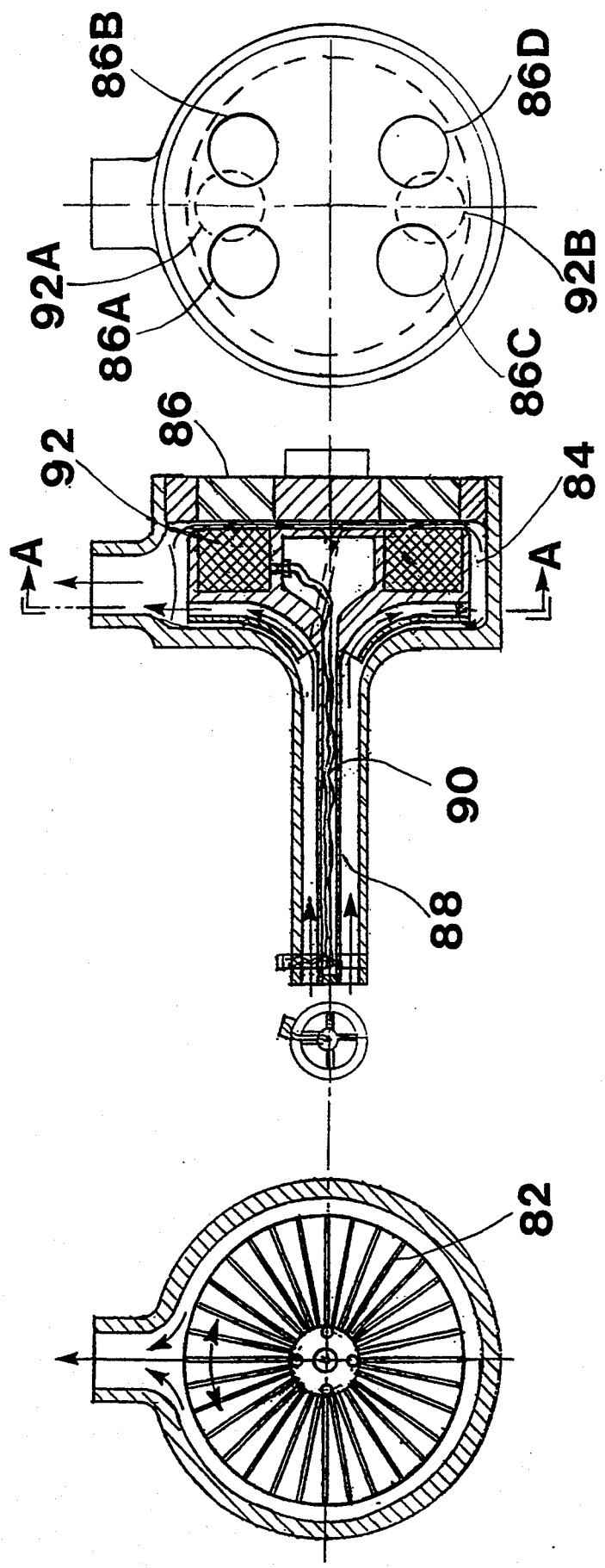
FIG. 2 is a sectional elevation view of a second embodiment of the invention.
FIG. 3 is an end view of the embodiment shown in FIG. 2.
FIG. 4 is a sectional view along line A—A in FIG. 2, further clarifying the construction shown in FIG. 2.

The embodiment of FIGS. 2, 3 and 4 shows a number of variations for the sake of illustration. These include the use of radial vanes 82, which can be seen in FIG. 4, a moving coil driver 84, interacting with stationary magnets 86, and a hollow torsion shaft 88, to permit the leading of wires 90 to the oscillating coils 92 without need of exposing them to the fluid. A covered impeller is again used, and a large number of radial vanes is used in the flow passages with small widths and heights so as to minimize losses due to circulation within the passages. Operation of the magnetic driver is the same as that shown in FIG. 1, except that the locations of the magnets and the coils are reversed. The use of moving coils is potentially advantageous because the coils can be made to be lighter than the magnets, thus reducing the inertia of the impeller and permitting use of a shaft at a lower spring rate, to obtain the same resonant frequency. This reduces hysteresis losses and the magnitude of any oscillatory force that may be transmitted to the support.

Referring to FIG. 3, it can be seen that the stator contains four permanent magnets, 86A, 86B, 86C and 86D, which interact with the two oscillating coils, 92A and 92B, which are driven by alternating current. Magnets 86A and 86B are of opposite polarity, and magnets 86C and 86D are of opposite polarity, such that when coil 92A is attracted by magnet 86A, it is repelled by magnet 86B, and, simultaneously, coil 92B is attracted by magnet 86D and repelled by magnet 86C.

Figures 5, 6, 7:
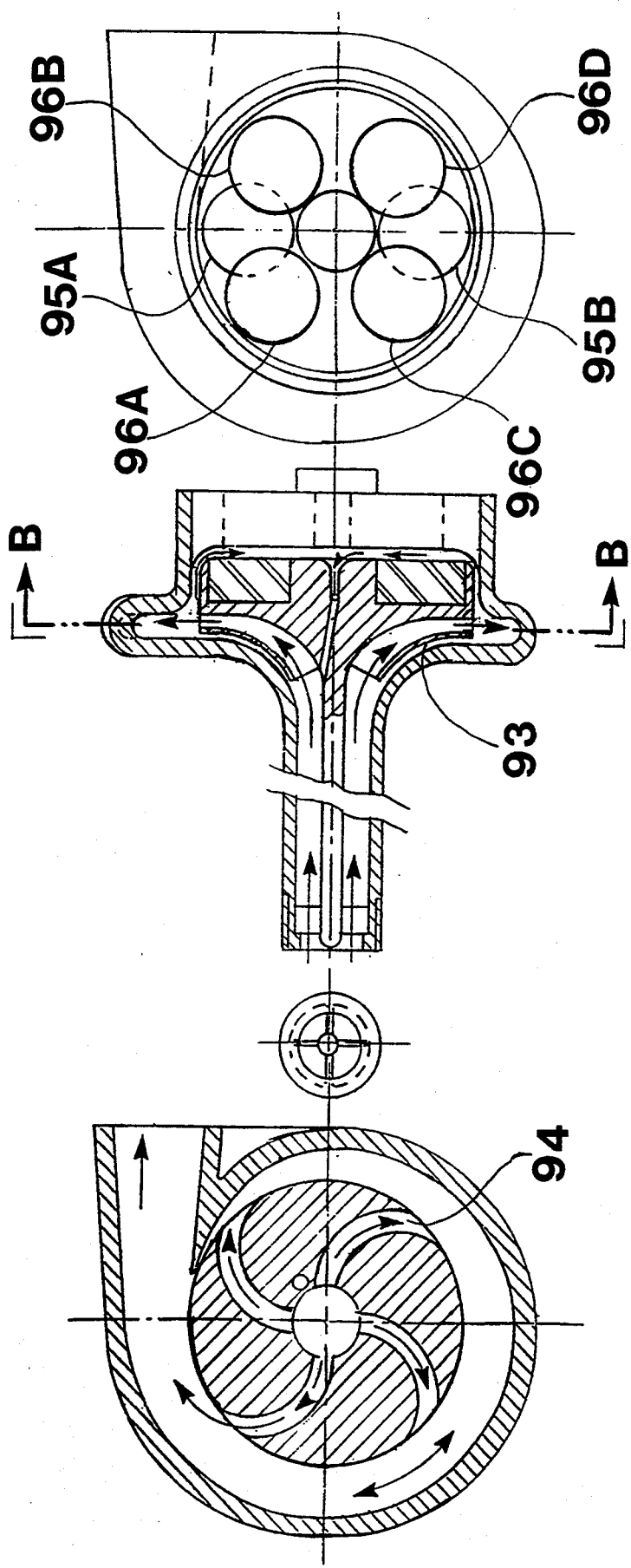
FIG. 5 is a sectional elevation view of a variation of the embodiment shown in FIG. 1.
FIG. 6 is an end view of the embodiment shown in FIG. 5, further clarifying the construction shown in FIG. 5.
FIG. 7 is a sectional view along line B—B in FIG. 5, further clarifying the construction shown in FIG. 5.

FIGS. 5, 6 and 7 show a variation of the oscillating centrifugal pump shown in FIG. 1, in which an impeller 93 is supported on a linear, solid, round torsion shaft. As seen in FIG. 7, which is a section along line B—B of FIG. 5, on the shaft end of the impeller there are a limited number of narrow and shallow flow passages 94, which are forward curved to increase the forward tangential velocity in the flow direction and to reduce the tangential velocity in the reverse direction to zero or a minimum, so as to result in a net average forward tangential velocity, with a degree of pressure recovery in the volute and diffuser to increase efficiency. Partial emission from the impeller is used to achieve high relative velocities and, consequently, a high forward tangential velocity. The flow passages 94 are distributed around the circumference to avoid unbalanced forces on the impeller 93. The impeller must be oscillated at torsional resonance to avoid large reactive torques, which would require excessively large magnetic driving elements and high reactive currents.

FIG. 6 shows the interactive arrangement of magnets 95A and 95 B, which are carried in the rotor 96, and stator coils 96A, 96B, 96C and 96D, which are driven by alternating current. Similar to the arrangement of FIG. 3, coils 96A and 96B are wound or excited to be simultaneously of opposite polarity, and coils 96C and 96D are also simultaneously of opposite polarity, such that when magnet 95A is attracted by coil 96A, it is repelled by coil 96B, and, simultaneously, magnet 95B is attracted by coil 96D and repelled by coil 96C. This is the same arrangement as that which is used in the preferred embodiment shown in FIG. 1.

Figure 8:
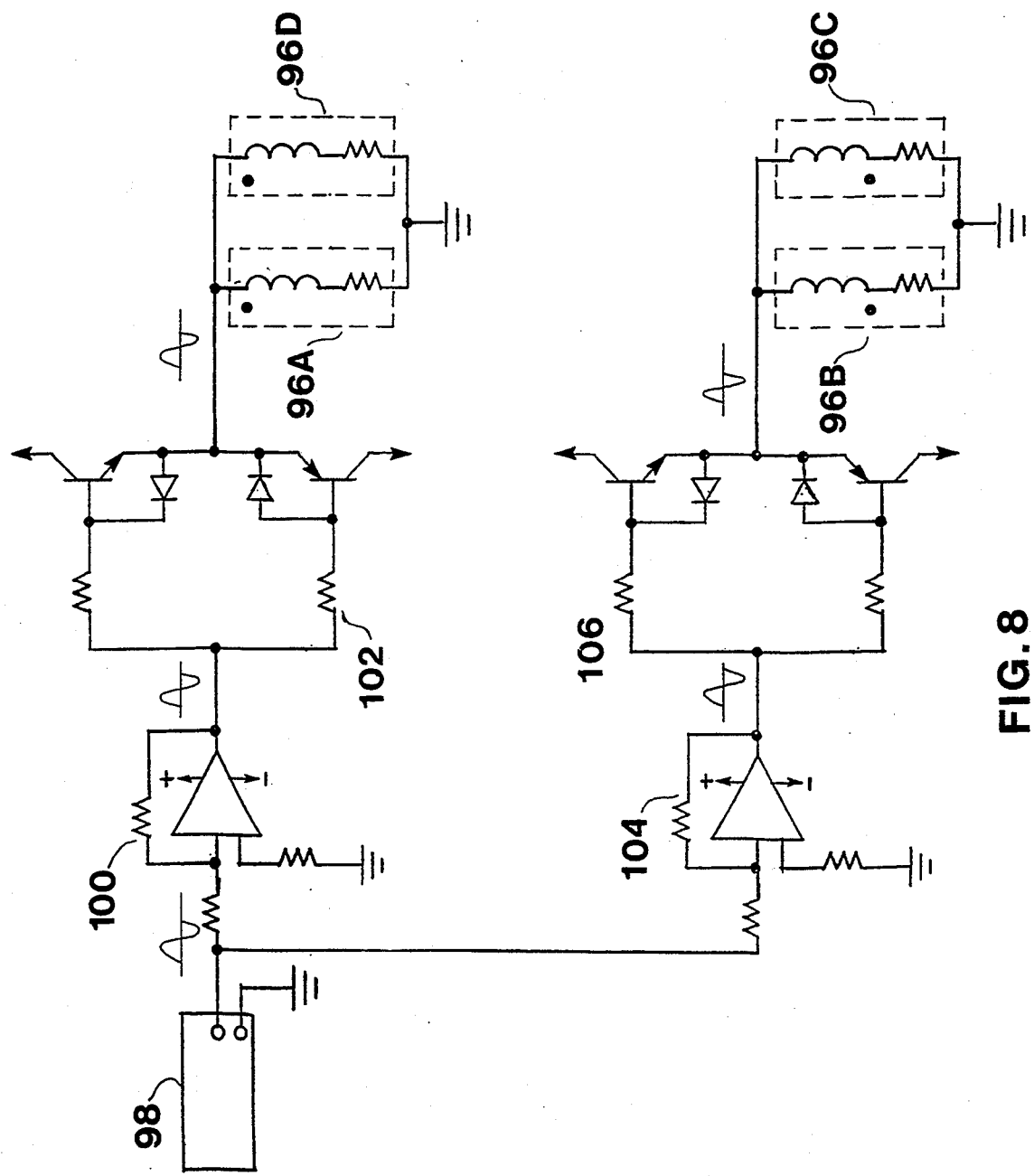
FIG. 8 is a schematic diagram of a circuit for driving the previous embodiments.

An electronic circuit for driving the previous embodiments, particularly those of FIG. 1 and FIG. 5, is shown in FIG. 8. This is connected as for driving the coils shown in FIGS. 5 and 6. As illustrated, coils 96A and 96D are wound to have one magnetic polarity, and coils 96B and 96C are wound to have an opposite magnetic polarity when all coils are excited by current having the same electrical polarity. It is to be understood that magnets 95A and 95B are oriented to have the same magnetic polarity. Signal generator 98 provides an AC signal at the torsional resonant frequency of the impeller and torsion shaft. This signal is amplified in voltage amplifiers 100 and 104 and bipolar power amplifiers 102 and 106, which supply amplified alternating currents to all the coils.

Figure 9:
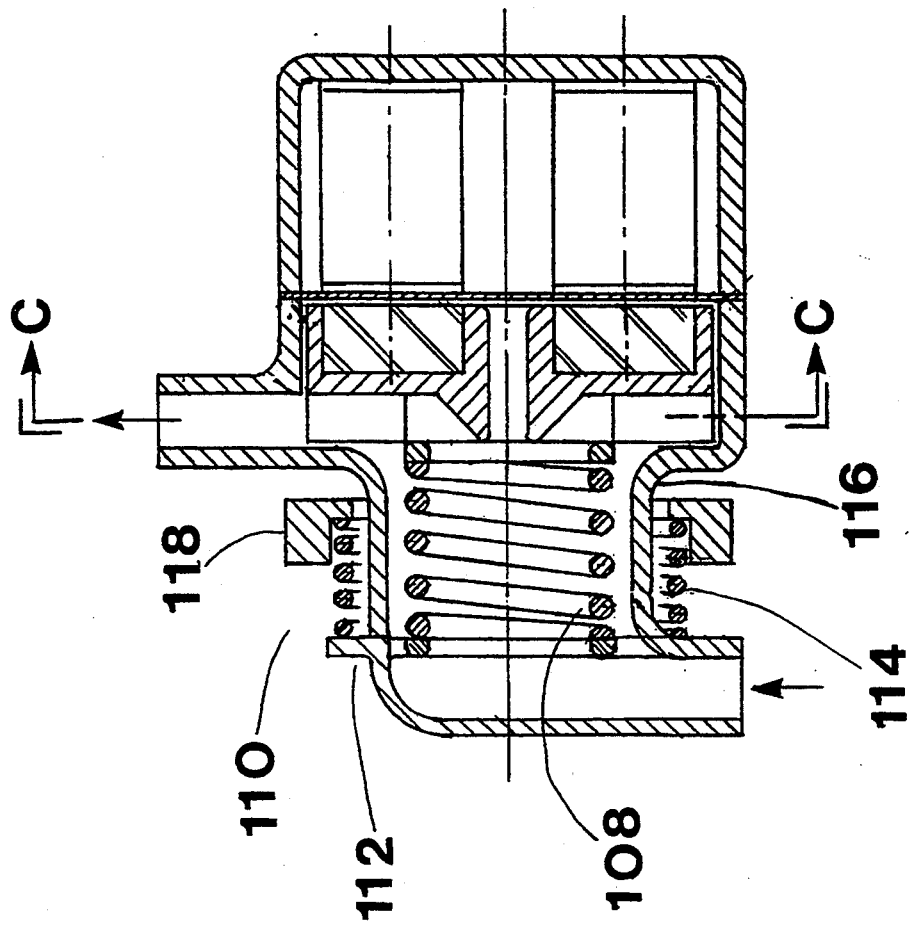
FIG. 9 is a sectional elevation view of another embodiment of the invention.
Figure 10:
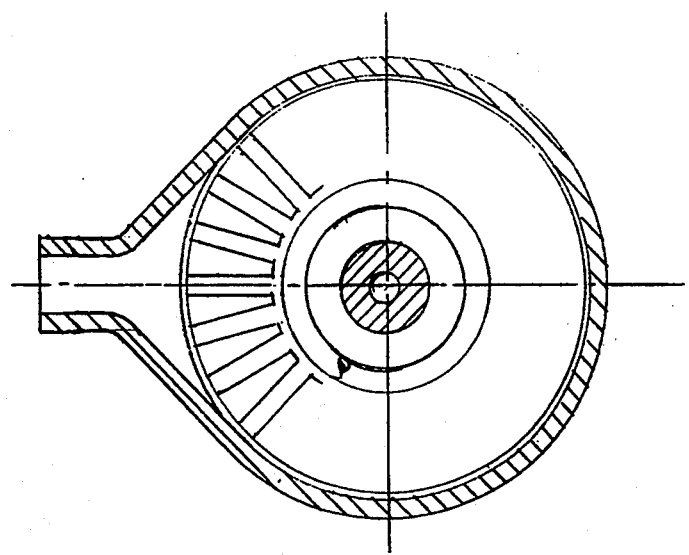
FIG. 10 is a sectional view along line C—C in FIG. 9, clarifying the construction shown in FIG. 9.

FIGS. 9 and 10 show a scale representation of an oscillating centrifugal pump which is similar to the embodiment of FIG. 1, except that the impeller is supported on a helical torsion spring 108 instead of a straight torsion shaft. The use of helical springs provides more freedom in design to achieve a compact assembly with an optimum combination of rotational excursion and stiffness. The torsion spring shown has the dimensions of a commercially available torsion spring (Associated Spring Co. No. T135-090-666). The rate of this spring is not sufficiently high, and it is anticipated that a special spring of approximately the same dimensions will be obtained. The overall dimensions of the pump are 2.5 in. diameter by 3.50 in. long. The oscillating frequency is 113 cps, and the angular excursion is +/−26 degrees. The oscillating system of the pump in FIG. 9 is unbalanced, and, therefore, some degree of vibration could be transmitted to the support, depending on the inertia of the stationary members. To avoid transmission of unwanted vibration, a dynamic vibration absorber 110 is anchored to the same support 112 as the oscillating impeller spring. The absorber consists of a torsion spring 114 about the inlet housing 116 and a freely oscillating inertia disk 118. The proportions of these members are not important, as long as the resonant frequency of the absorber is the same as that of the impeller-torsion spring system.

It has been concluded from tests that have been conducted with experimental oscillating centrifugal pumps, that transmitted vibration from an oscillating centrifugal pump can be eliminated or reduced to an acceptable level by either driven torque balancing or a passive dynamic vibration absorber. The dynamic vibration absorber has advantages in that is does not consume power, and the only requirement is that it must have the same resonant frequency as the oscillator driving frequency so that small elements can be used, mounted conveniently on the structure.

Figures 11, 12:
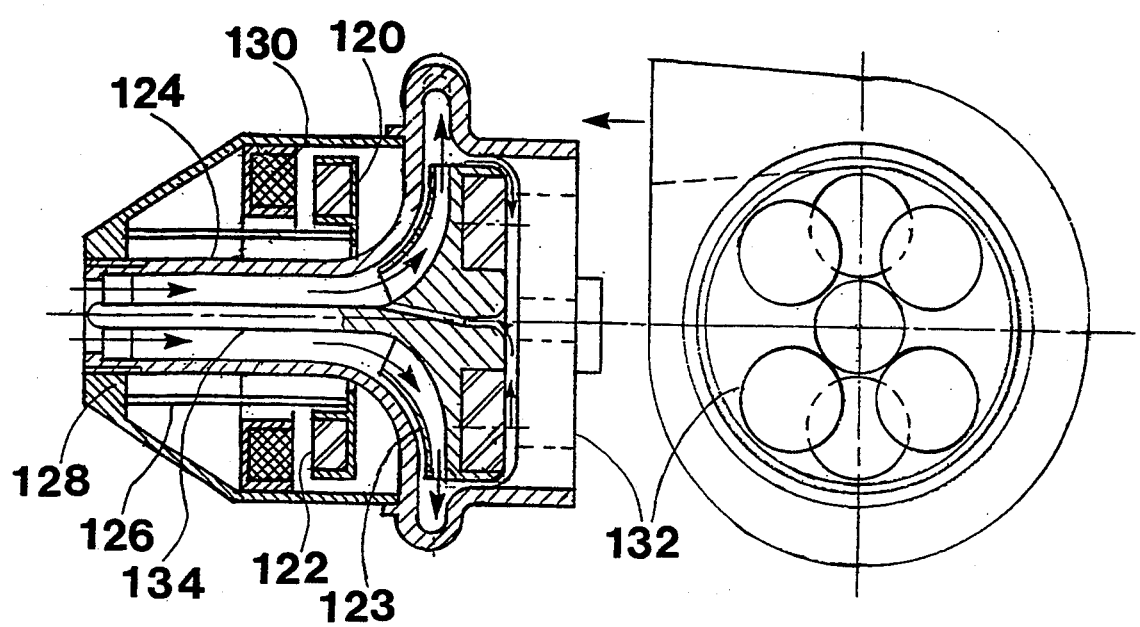
FIG. 11 is a sectional elevation view of another variation of the embodiment shown in FIG. 1.
FIG. 12 is an end view of the embodiment shown in FIG. 11.

FIGS. 11 and 12 show the oscillating centrifugal pump of FIG. 1, modified for the inclusion of vibration eliminating means. An oscillating balance disc 120 with two permanent magnets 122, similar to the arrangement of the oscillating impeller 123, is suspended co-axially with the pump housing 124, and suspended on four rods 126 which are anchored in the same plane 128 as the impeller torsion shaft. The magnets 122 of the balance disc 120 are driven by four stationary coils 130, in similar arrangement to the impeller drive coils 132, in contra-oscillation with the impeller. The balancing components are proportioned to be smaller than the oscillating impeller assembly, but the resonant frequency is identical and the spring stiffness and angular displacement are selected and controlled so that the balancing torque at the support plane is equal and opposite to that transmitted by the impeller torsion shaft 134. It is evident that, if the driving frequency is constant, or varied only over a sufficiently narrow band, that the oscillating driven torque balancer could be replaced by a dynamic vibration absorber, in which case the balance drive magnets and coils could be eliminated, simplifying the construction. It should be noted that the axial flow inlet of FIG. 1 is retained in FIG. 11.

There are certain limitations of an oscillating impeller compared to a unidirectionally rotating impeller. In the worst case, with radial vanes and symmetrical geometry and action, there is no pressure recovery from the tangential component of absolute velocity; the entire pressure rise is due to centrifugal forces. Also, in an oscillation the tip velocity is zero at the end points of the oscillation. Compliance in the systems could store pressure energy so that there could be a minimum pressure level (e.g. elastolic) at the end points, which would cause backflow through the impeller channels until the tip velocity reaches a value at which the centrifugal pressure exceeds the minimum stored back pressure.

Figure 13:
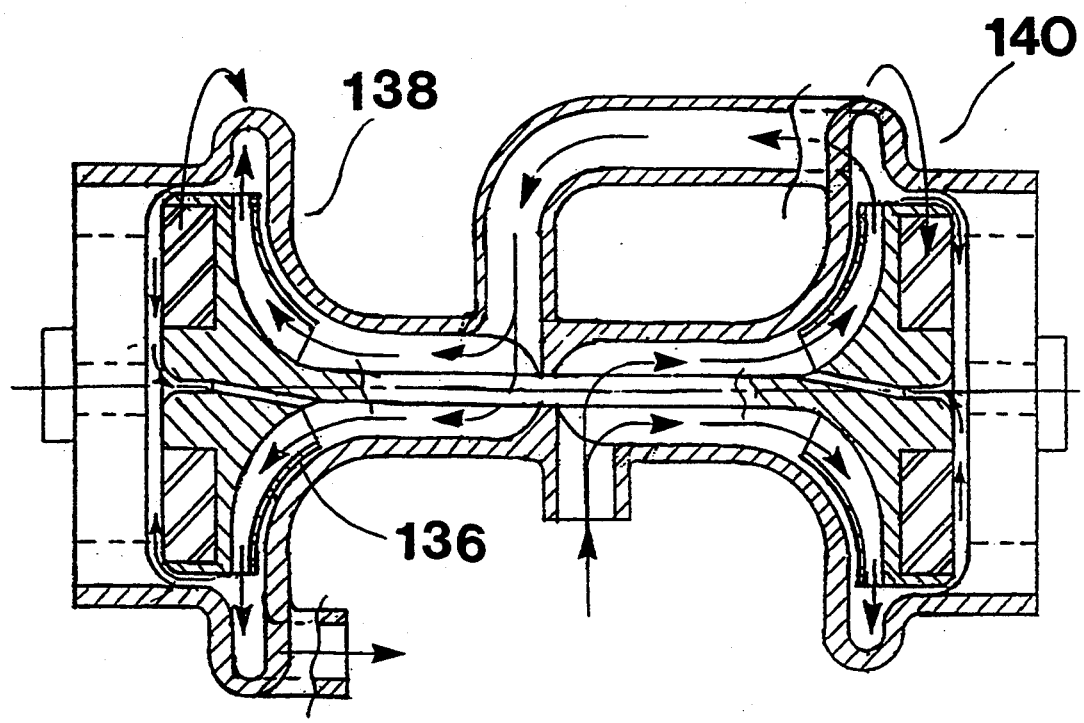
FIG. 13 is another embodiment of the invention, illustrating two-stage operation.

The balanced two-stage oscillating blood pump concept illustrated in FIG. 13 utilizes the driven, contra-oscillating vibration balance configuration shown in FIG. 11. Here, however, the inactive oscillating balance disc is replaced by the active impeller 136 of a second, oscillating centrifugal pumping stage 138, identical but opposite to the first stage 140. In addition to providing inherent vibration balancing, the two-stage configuration provides design flexibility, and the benefit of allowing relaxation of some parameters, such as oscillation frequency and amplitude, which could reduce the stress level of the torsion shaft. The possible disadvantages of the two-stage oscillating blood pump are increased length (but not necessarily double), a somewhat more costly disposable element, and increased priming volume.

A potential advantage of using two pumping stages connected in series is that if the two stages are oscillated in quadrature phase relation, back flow is eliminated and performance is substantially improved. Vibration balancing, however, is not achieved with a 90 degree oscillatory phase difference, and a dynamic vibration absorber would be required.

Figure 14:
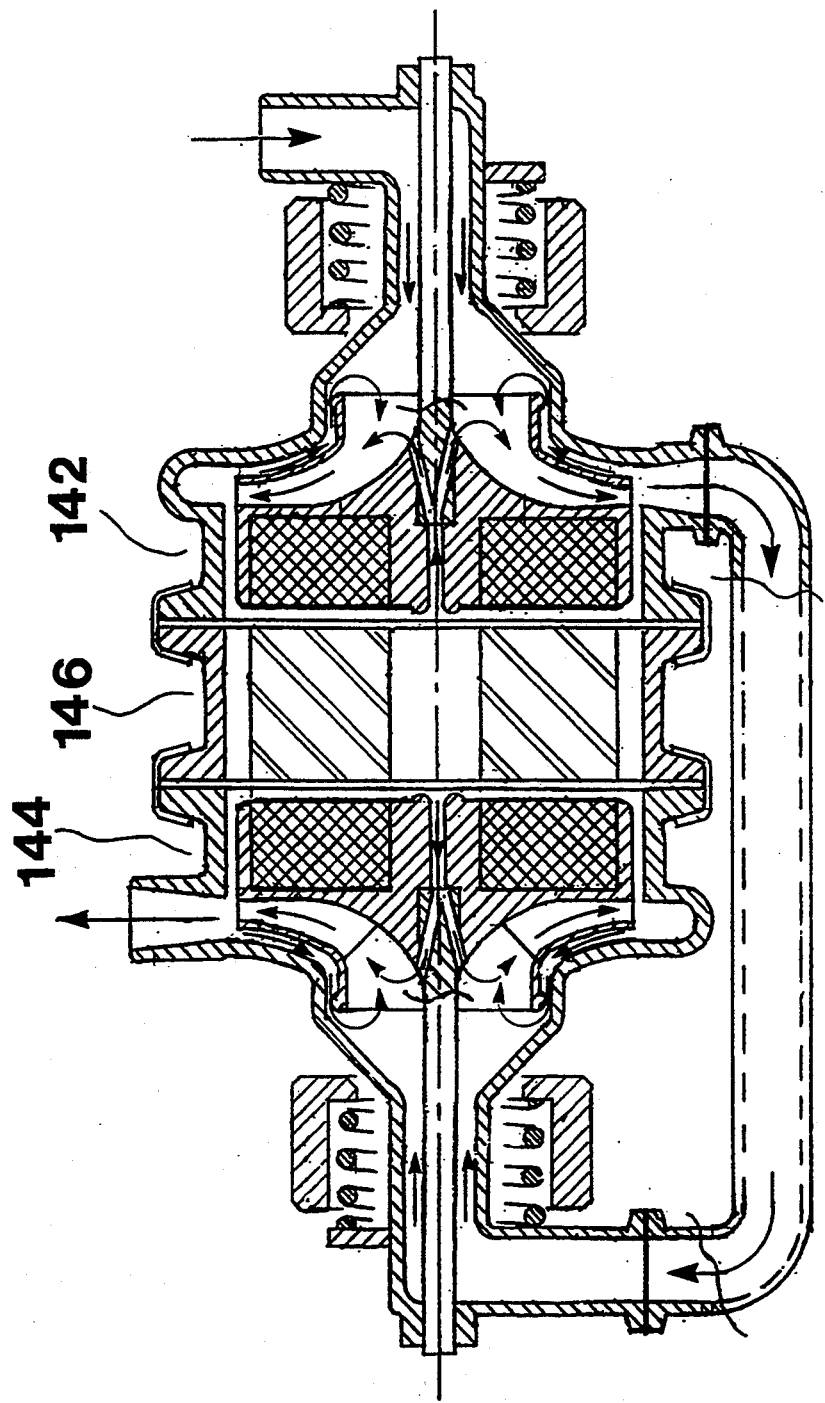
FIG. 14 is a variation of the embodiment shown in FIG. 13.

FIG. 14 is an adaptation of the design of the practical oscillating element shown in FIG. 1, into a two-stage pumping assembly. The two-stage unit consists of two opposed single stage oscillating element assemblies 142, 144 fastened on opposite sides of a detachable drive unit 146. If the rotors of the two stages were to be driven in phase coincidence, or in 180 degree phase relation, the same drive arrangement that is shown in FIG. 1 could be utilized; that is, the rotor could contain the two drive magnets and the detachable drive unit would contain the four drive coils. An economy is realized because only one detachable drive unit is required. Such an arrangement would be advantageous where the amount of energy loss due to backflow in the rotor is not critical, or if other mechanisms in the rotor could be used to eliminate backflow.

One of the advantages of two-stage operation is that, if the two impellets are oscillated in a 90 degree phase relation, backflow is eliminated. The 90 degree phase relation cannot be achieved by a single set of stationary drive coils interacting with rotor magnets, however; and, therefore, FIG. 14 has four permanent magnets located in the detachable drive unit, and two drive coils In each of the oscillating rotors. The proper phase relation can be achieved by independent excitation of the two sets of drive coils. For the same overall pressure rise that is achieved with a single stage element, each stage of the two-stage element generates half the total pressure rise, and, therefore, the impeller tip velocity and the oscillation angle can be reduced. This permits use of a shorter torsional drive shaft, which is illustrated in FIG. 14, so that the overall length of the two-stage assembly (7 inches) is only one inch longer than a single stage element, and the overall diameters are the same.

Figure 15:
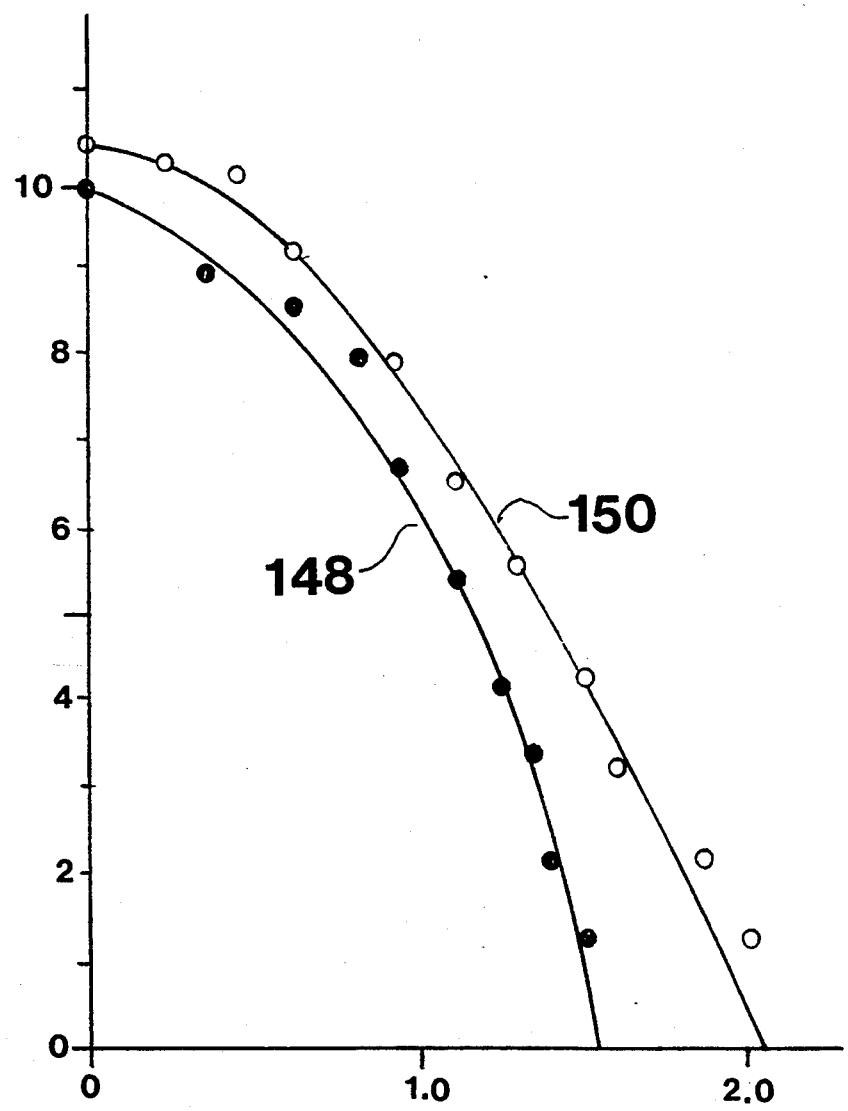
FIG. 15 is a plot of performance of the two-stage embodiment in FIG. 13, illustrating the effects of phase.

To confirm the existence of backflow at the oscillation end points, and to determine the effectiveness of two stage phase quadrature to reduce or eliminate it, both stages of an experimental two-stage oscillating centrifugal pump were excited at the same frequency, which was set half-way between the Individual resonances, first with a 180 degree phase shift, then with a 90 degree phase shift. The resulting characteristics are shown plotted in FIG. 15. It is seen that flow rates from the 180 degree phase shift plot 148 are 20 to 25% less than those from the 90 degree phase shift plot 150, confirming the existence of backflow, and the effectiveness of the phase shift to reduce it.

Figure 16:
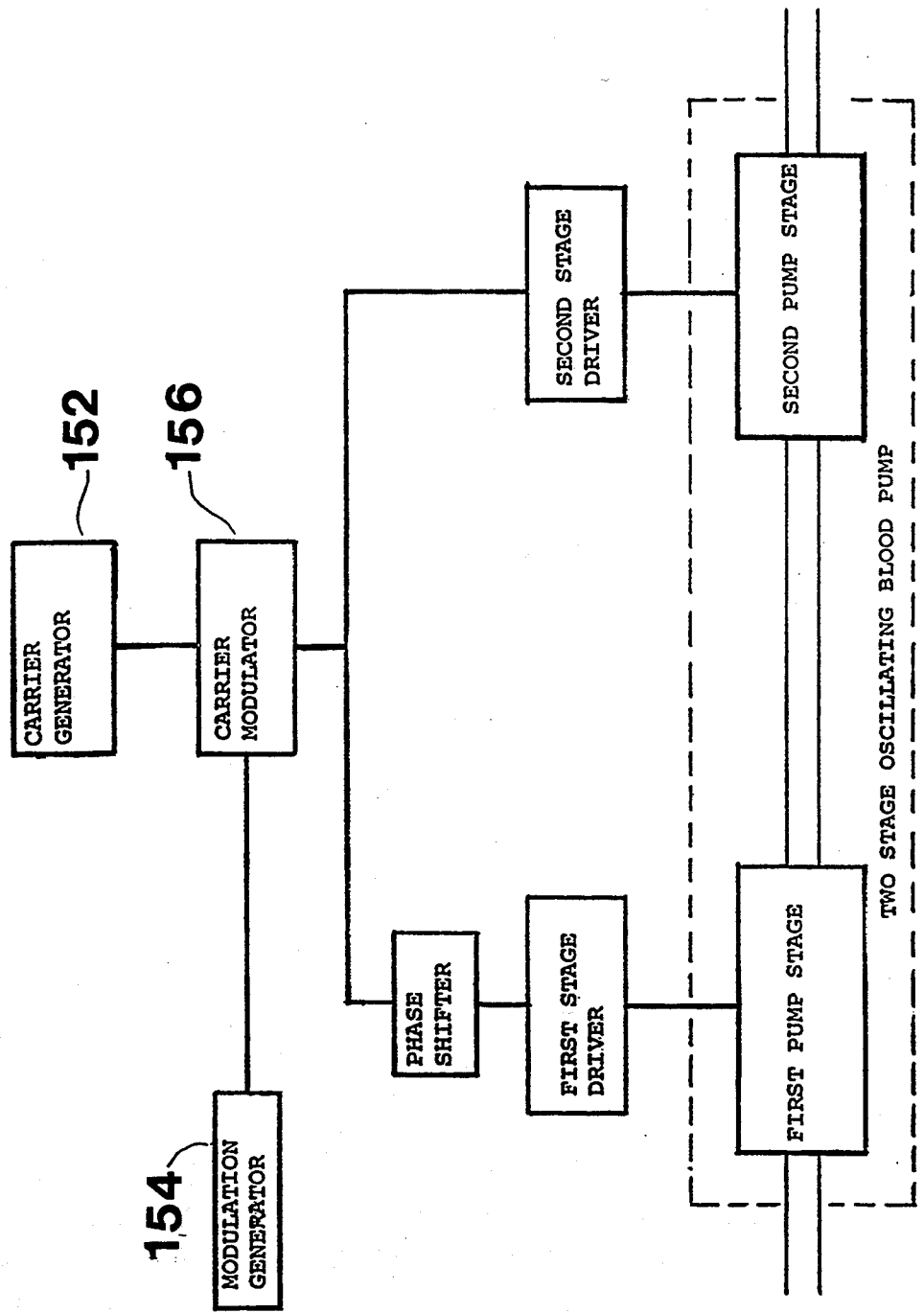
FIG. 16 is a block diagram of a two-stage system.

FIG. 16 is a block diagram of a two-stage oscillating centrifugal pumping system. Of interest here is the inclusion of a 90 degree phase shifter, which permits the two series-connected pumping stages to be oscillated in phase relations of 180 degrees or 90 degrees, in order to alleviate the effects of backflow at the end points of the oscillation.

For use as a circulatory assist blood pump it would be advantageous for the oscillating centrifugal pump to be capable of pulsarlie as well as continuous operation. The ability of an experimental oscillating centrifugal pump to provide pulsattle flow by modulation of the resonant frequency driving current has been demonstrated. The system of FIG. 16 has provision for pulsattle operation. A signal at the impeller oscillation frequency is produced in a carrier generator 152, and a signal at pulse recurrence frequency is produced in a modulation generator 154 and supplied to a carrier modulator 156 to modulate the impeller oscillation in a pulsattle fashion.

To avoid backflow during diastole, the pump is not shut off cyclically, but the output pressure is varied between systolic and system diastolic levels. A control is included to adjust the diastolic pressure level. The system response should not be sufficiently fast to cause excessive dp/dt rates, and, consequently, square wave modulation is adequate.

Figure 17:
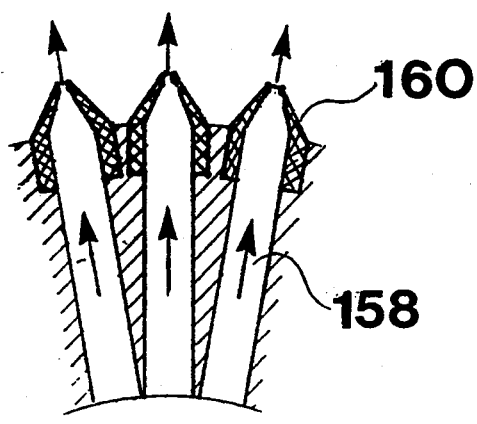
FIGS. 17 and 18 explain the operation of one means of preventing backflow.
Figure 18:
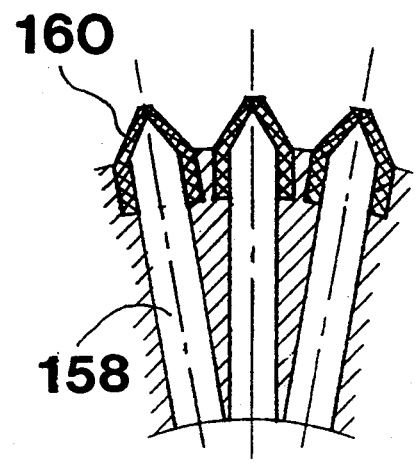

A means for the prevention of backflow through the impeller channels is presented in FIGS. 17 and 18. As shown in these illustrations, the outer, discharge, end of each impeller channel 158 is terminated in a molded (e.g. polyurethane) unidirectional valve 160, which is similar to well-known duck-bill valves. FIG. 17 illustrates the condition at the mid-point of oscillation in either direction when the tip velocity is maximum, and there is free outward flow through the valves. In FIG. 18 the oscillation is at one of the end points, when the tip velocity is zero and there is no outflow. Compliance pressure in the outlet causes the valve tips to close, preventing backflow through the channels. There should be no stagnant regions at the exterior of the valve tips, as might be the case where duck-bill valves are located in a tubular line, because the valve tips extend into an open plenum, and the oscillatory motion will produce currents within and past the spaces between the valves.

Although backflow has been shown to be eliminated by two-stage operation with oscillation in quadrature, other factors being equal, it would be more desirable if backflow could be eliminated or minimized by the configuration of a single stage element. An alternate design for an impeller check valve is shown in FIGS. 19-21. In this design, a very light leaf spring 162 extends the length of a radial flow channel 164 in the impeller 166. The leaf spring is anchored at the top of the channel at its entrance (eye) 168, and it is bent to be normally closed 170, touching the hub 170 of the impeller at the outlet 172. At the center of oscillation, when the tip velocity is greatest, the centrifugal pressure is greatest, and it forces the leaf spring to open and the fluid to flow radially outward. At the ends of the oscillation cycle, there is no centrifugal field and no radial outflow, and the leaf spring is closed. The spring force can be very low, because any pressure existing in the outlet that would normally cause reverse flow in the impeller channel will also force the leaf spring against the hub, effectively checking reverse flow.

As a practical design, the impeller cover would have two layers; the first, in contact with the blades, would be a very light compatible metal or plastic sheet 174 with fingers 176 cut in to form leaf springs in the channel. This sheet would itself be held by an outer cover 178, which would have slots 180 slightly smaller than the width of the leaf spring so that, during outflow, it would be retained and could not be forced against the wall of the housing. Such leaf spring cheek valves have been used in diaphragm pumps at 60-70 cps and in reciprocating solenoid pumps at 120 cps, among other examples.

What is claimed is:

1. An oscillating centrifugal pump, comprising:
   (a) a housing with a longitudinal axis, having a front end and a rear end, spaced apart on said axis, said housing including a pumping chamber within and at the front end of said housing, said pumping chamber being defined by a continuous transverse front wall to close said pumping chamber at said front end of the housing, a transverse rear wall with a central opening, axially-spaced from said transverse front wall, and a longitudinal closed side wall, between said front and rear transverse walls, said housing being closed except for an inlet in said housing, outside of, and axially spaced from said pumping chamber, and an outlet in the longitudinal side wall of said pumping chamber, said housing being free of mechanical bearings, flexing or rubbing external seals, or apertures leading to the exterior of the housing except for said inlet and outlet,
   (b) an impeller in said pumping chamber, said impeller having an axial inlet and a radial outlet and a flow passage between said impeller inlet and outlet, said impeller being mounted on an elastic support, which provides limited freedom of angular oscillation for said impeller about the longitudinal axis of said housing, said elastic support being a torsion member within said housing with a front, oscillating, end connected to said impeller, and a rear, stationary, end connected to said housing, said impeller also containing a magnetic element, and
   (c) magnetic means external to said housing including an external magnetic element to interact with said magnetic element contained in said impeller and to drive said impeller in an angular oscillation about the longitudinal axis within said pumping chamber by magnetic action through the walls of said pumping chamber.

2. An oscillating centrifugal pump as claimed in claim 1, in which said torsion member within said housing is a torsion shaft with a front, oscillating, end connected to the impeller, and a rear, stationary, end connected to the housing.

3. An oscillating centrifugal pump as claimed in claim 1, in which said torsion member within said housing includes a coil spring with a front, oscillating, end connected to the impeller, and a rear, stationary, end connected to the housing.

4. An oscillating centrifugal pump as claimed in claim 1, in which said flow passage between said impeller inlet and outlet is a radial flow passage.

5. An oscillating centrifugal pump as claimed in claim 1, in which said flow passage between said impeller inlet and outlet is forward curved to increase the forward tangential velocity in the preferred direction of impeller outlet flow.

6. An oscillating centrifugal pump as claimed in claim 1, including an external disc supported by an external torsion member, having equal mass and stiffness, and being co-axial and opposite to said impeller and said torsion member within said housing, and means to drive said external disc in an angular oscillation that is equal and opposite to the angular oscillation of said impeller, to balance vibrations caused by the angular oscillation.

7. An oscillating centrifugal pump as claimed in claim 1, in which said housing, said impeller and said elastic support comprise a unitary, sealed, replaceable pumping element.

8. An oscillating centrifugal pump as claimed in claim 1, in which said external magnetic driving means drives the impeller at the torsional resonant frequency of said impeller mounted on said elastic support.

9. An oscillating centrifugal pump as claimed in claim 8, including an external mass mounted on an external elastic support that is connected to the housing, said external mass and said external elastic support having a torsional resonant frequency that is equal to the torsional resonant frequency of said internal impeller mount on its elastic support.

10. An oscillating centrifugal pump as claimed in claim 1, including means to eliminate back flow through the impeller at the end points of oscillation, when the impeller tip velocity is zero.

11. An oscillating centrifugal pump as claimed in claim 10, in which said back flow eliminating means includes a second oscillating centrifugal pump, hydraulically connected in series with said housing, and containing a second impeller mounted on a second torsion member and means to oscillate the second impeller at the same frequency as said impeller in said housing, but at a 90 degree phase relation so that when said impeller in said housing is at the end point of its oscillation, the second impeller is at the mid point of its oscillation, to sustain pumping action and to prevent back flow.

12. An oscillating centrifugal pump as claimed in claim 10, in which said back flow eliminating means is an impeller check valve consisting of a leaf spring that extends the length of a flow channel in said impeller, said leaf spring being anchored at the top of said channel at its entrance and being bent to be normally closed, touching the hub of said impeller at its outlet, so that fluid flowing radially outward forces the leaf spring to open in an axial direction.

13. An oscillating centrifugal pump as claimed in claim 1, in which said external magnetic element included in said external magnetic driving means includes an electromagnetic coil.

14. An oscillating centrifugal pump as claimed in claim 1, in which said magnetic element contained in said impeller includes an electromagnetic coil.

15. An oscillating centrifugal pump as claimed in claims 13 or 14, including electrical means to drive the electromagnetic coil in either the impeller or the magnetic driving means with an alternating current at the oscillation frequency, and to modulate said oscillation frequency so as to provide pulsatile flow from said oscillating centrifugal pump at said modulation frequency.

16. An oscillating centrifugal pump as claimed in claim 13, in which said external magnetic element includes a second electromagnetic coil, and means to drive the two coils in opposition, so that the first coil applies an attractive force to said impeller magnetic element when the second coil applies a repulsive force to said impeller magnetic element.

17. An oscillating centrifugal pump, comprising:
 (a) a housing with a longitudinal axis, said housing having a front end and a rear end spaced apart on the axis,
 (b) a pumping chamber at the front end of said housing, said pumping chamber being defined by a continuous, transverse front wall to close said pumping chamber at said front end of the housing, a transverse rear wall with a central opening, axially-spaced from said transverse front wall, and a longitudinal co-axial side wall, between said front and rear transverse walls,
 (c) an outlet in the longitudinal side wall of said pumping chamber,
 (d) an inlet in said housing, outside of, and axially spaced from, said pumping chamber, said housing being free of bearings, flexing seals or apertures leading to the exterior of the housing except for said inlet and outlet,
 (e) an impeller in said pumping chamber, said impeller being mounted on an elastic support, which provides limited freedom of angular rotation for said impeller in either direction about the longitudinal axis of said housing and
 (f) magnetic means external to said housing to drive said impeller in an angular oscillation about the longitudinal axis within said pumping chamber at the torsional resonant frequency of said impeller mounted on said elastic support by magnetic action through the walls of said housing.

18. An oscillating centrifugal pump as claimed in claim 17, including an external mass mounted on an external elastic support that is connected to the housing, said external mass and said external elastic support having a torsional resonant frequency that is equal to the torsional resonant frequency of said internal impeller mounted on its elastic support.

19. An oscillating centrifugal pump, which consists essentially of:
 (a) a housing with a longitudinal axis, having a front end and a rear end, spaced apart on said axis, said housing including a pumping chamber within and at the front end of said housing, said pumping chamber being defined by a continuous transverse front wall to close said pumping chamber at said front end of the housing, a transverse rear wall with a central opening, axially-spaced from said transverse front wall, and a longitudinal closed side wall, between said front and rear transverse walls, said housing being closed except for an inlet in said housing, outside of, and axially spaced from said pumping chamber, and an outlet in the longitudinal side wall of said pumping chamber, said housing being free of mechanical bearings, flexing or rubbing external seals, or apertures leading to the exterior of the housing except for said inlet and outlet,
 (b) an impeller in said pumping chamber, said impeller having an axial inlet and a radial outlet and a flow passage between said impeller inlet and outlet, said impeller being mounted on an elastic support, which provides limited freedom of angular oscillation for said impeller about the longitudinal axis of said housing, said elastic support being a torsion member within said housing with a front, oscillating, end connected to said impeller, and a rear, stationary, end connected to said housing, said impeller also containing a magnetic element, and
(c) magnetic means external to said housing including an external magnetic element to interact with said magnetic element contained in said impeller and to drive said impeller in an angular oscillation about the longitudinal axis within said pumping chamber by magnetic action through the walls of said pumping chamber.

* * * * *